(12) United States Patent
Martin

(10) Patent No.: US 6,231,505 B1
(45) Date of Patent: May 15, 2001

(54) LARYNGOSCOPE BLADE

(76) Inventor: Tyson Edward Martin, P.O. Box 130878, Tampa, FL (US) 33681

( * ) Notice: Subject to any disclaimer, the term of this patent is extended or adjusted under 35 U.S.C. 154(b) by 0 days.

(21) Appl. No.: 09/398,715

(22) Filed: Sep. 20, 1999

(51) Int. Cl.$^7$ .................................................. A61B 1/267
(52) U.S. Cl. ........................................... 600/194; 600/190
(58) Field of Search ..................... 600/185, 190, 600/191, 192, 194, 197, 199

(56) References Cited

U.S. PATENT DOCUMENTS

| | | | |
|---|---|---|---|
| 2,026,065 | * | 12/1935 | Rohr . |
| 2,765,785 | * | 10/1956 | Pagoto . |
| 3,890,960 | * | 6/1975 | Wunsch et al. . |
| 3,943,920 | * | 3/1976 | Kandel . |
| 5,003,962 | * | 4/1991 | Choi . |
| 5,065,738 | * | 11/1991 | Van Dam . |
| 5,575,758 | * | 11/1996 | Fasterbrook, III . |
| 5,702,351 | * | 12/1997 | Bar-Or et al. . |
| 5,888,195 | * | 3/1999 | Schneider . |
| 5,984,863 | * | 11/1999 | Ansari . |
| 6,045,499 | * | 4/2000 | Pitesky . |

FOREIGN PATENT DOCUMENTS

206542 * 11/1939 (CH) ................................. 606/248

* cited by examiner

Primary Examiner—Paul J. Hirsch
(74) Attorney, Agent, or Firm—Pettis & Van Royen, P.A.

(57) ABSTRACT

The present invention relates to a laryngoscope blade used to assist practitioners in endotracheal intubation. The blade comprises a longitudinally extending member that has a first end and a second end. The member has a planar lingual surface, a palatal surface and a pair of opposed longitudinal edges. A pair of rails extend outwardly from the planar lingual surface of the member. An element extends outwardly from the palatal surface proximal to one of the longitudinal edges of the pair of edges. A portion of the element overlies and is spaced apart from the palatal surface. A coupler is attached to the first end of the member for attachment to a handle.

7 Claims, 2 Drawing Sheets

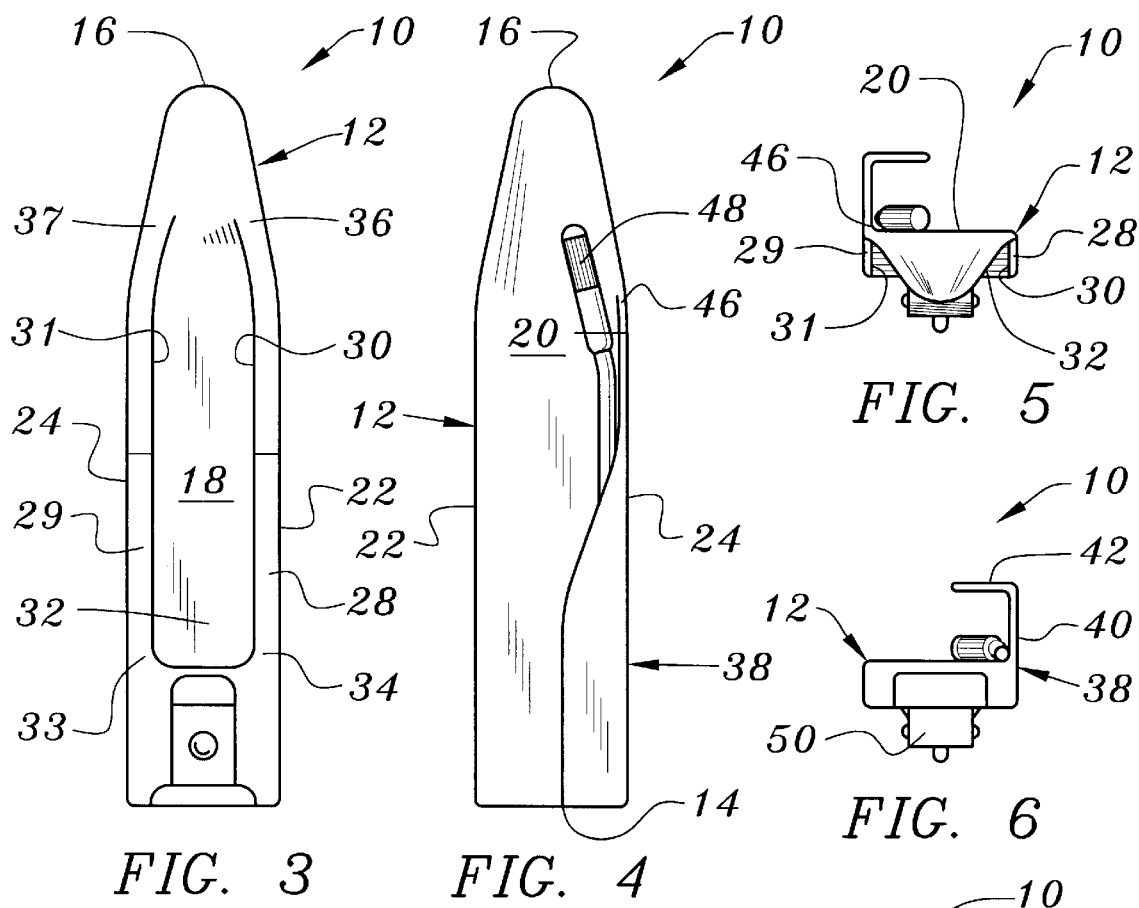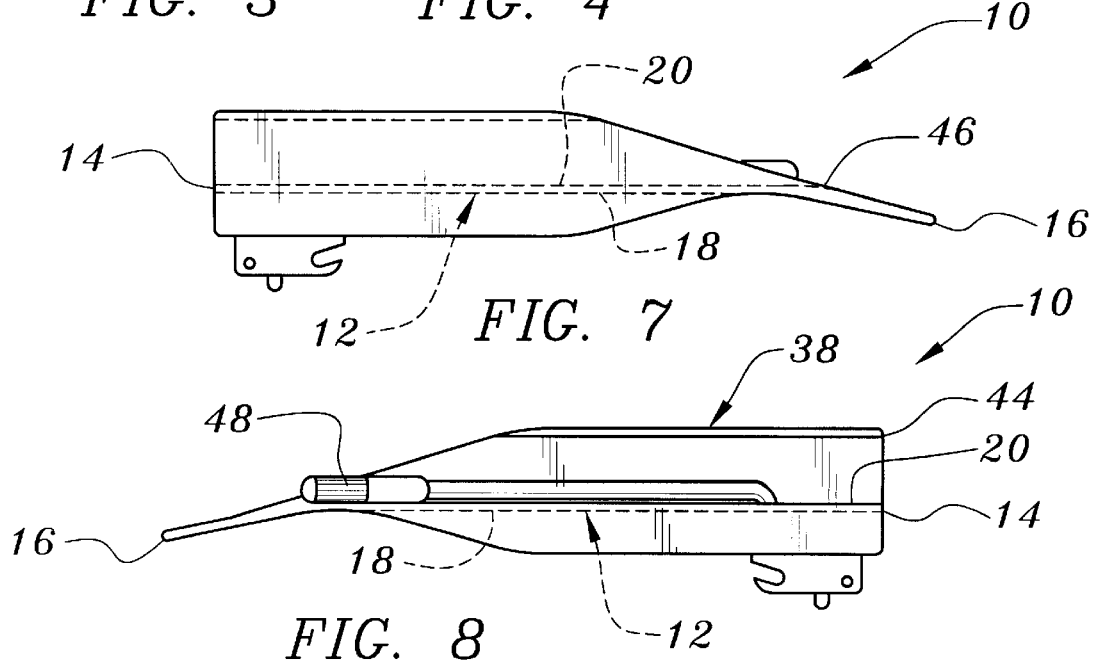

LARYNGOSCOPE BLADE

BACKGROUND OF INVENTION

1. Field of the Invention

The present invention relates to a medical apparatus known as a laryngoscope that is used to facilitate endotracheal intubation of a patient. Intubating a patient provides an airway when the patient requires assistance in breathing. The laryngoscope may also be used to assist in the examination of the larynx and surrounding area.

2. Description of the Prior Art

Laryngoscopes are well-known in the art and have been used to assist in intubating patients during emergency situations to provide resuscitation or mechanical ventilation. Laryngoscopes are also used in a more controlled environment, for example in preparation for surgery. Intubation requires the insertion of a flexible tube through the oral cavity, the oropharynx, and into the trachea. It is essential that the practitioner inserting the tube have a clear view of the epiglottis and the vocal chords to enable the practitioner to guide the tube into the trachea without injury to the patient.

A standard laryngoscope comprises a stainless steel handle and a laryngoscope blade. The handle houses batteries as a power source for a light that is attached to the blade. One end of the laryngoscope blade is releasably secured at a generally right angle to the handle. The attachment point closes the electrical connection between the battery and the light. The practitioner inserts the blade into the throat through the oral opening with the aid of the light which is attached proximal to the other end of the blade.

There are many factors that come into play when someone is being intubated, but the most important factor is an unobstructed view of the patient's vocal chords which lie at the entrance to the trachea where the tube is to be inserted. The two most common laryngoscope blades available are the Miller blade, which is disclosed in U.S. Pat. No. 5,065,738 issued to Van Dam, and the Macintosh blade, which is disclosed in U.S. Pat. No. 2,354,471 issued to R. R. Macintosh.

The Miller blade is a straight blade that has a round tubular shape and a small diameter. The Miller blade has a longitudinal axis which generally coincides with the line of sight used during intubation. The blade is concave in relation to the longitudinal axis and the exterior surface of the concave portion of the blade contacts the tongue of the patient during intubation. As the blade is concave, the patient's tongue easily moves around the blade obstructing the view of the oropharynx. When the tongue is free to move, the patient also uses his tongue in an attempt to eject the blade from his mouth making intubation difficult. In addition, the maximum distance between the flange 38 of the Miller blade and its concave upper surface 42, vertical spacing, is small, such that when a patient bites on the blade, the blade cannot keep the mouth open wide enough for the practitioner to easily see the vocal chords.

The Macintosh blade has a longitudinal axis that is curved throughout most of its length. Viewing the vocal chord area through a curved blade is like trying to look around a bend in the road when driving a car. The Macintosh blade has a wide and flat cross-section, unlike the Miller blade and controls the tongue better but the patient can still move his tongue around the blade and obstruct the practitioner's view of the chords. When a patient's epiglottis is anterior the neck, closer to the front of the neck, it requires extreme lift force be applied to the tongue and surrounding tissues to move the epiglottis away from the line of sight and thus overcome the loss of sight attributed to the curve of the blade.

Notwithstanding the existence of such prior art blades, it remains clear that there is a need for blades that can better control the patient's tongue, provide a clearer view of the oropharynx and the vocal chords and cause less damage to the surrounding tissue of the patient.

SUMMARY OF THE INVENTION

The present invention relates to a laryngoscope blade used to assist practitioners in endotracheal intubation of the compliant patient as well as a patient that is resisting the insertion of the laryngoscope and the endotracheal tube. Most simply stated, the blade comprises a longitudinally extending member that has a first end and a second end. The member has a lingual surface, a palatal surface and a pair of opposed longitudinal edges. A pair of rails extend outwardly from the lingual surface of the member. One of the pair of rails is proximal to one of the pair of edges, and the other rail is proximal to the other one of the pair of edges of the member. An element extends outwardly from the palatal surface proximal to one of the longitudinal edges of the pair of edges. A portion of the element overlies and is spaced apart from the palatal surface. A coupler is attached to the first end of the member for attachment to a handle.

The invention accordingly comprises an article of manufacturer possessing the features, properties, and the relation to elements which will be exemplified in the article hereinafter described, and the scope of the invention will be indicated in the claims.

BRIEF DESCRIPTION OF THE DRAWINGS

For a fuller understanding of the nature and objects of the invention, reference should be had to the following detailed description taken in connection with the accompanying drawings, in which:

FIG. 3 is a bottom plan view of the invention of FIG. 1;

FIG. 4 is a top plan view of the invention of FIG. 1;

FIG. 5 is a front elevational view of the invention of FIG. 1;

FIG. 6 is a rear elevational view of the invention of FIG. 1;

FIG. 7 is a left side elevational view of the invention of FIG. 1; and

FIG. 8 is a right side elevational view of the invention of FIG. 1.

Similar reference characters refer to similar parts throughout the several views of the drawings.

DETAILED DESCRIPTION OF THE INVENTION

Figure 1:
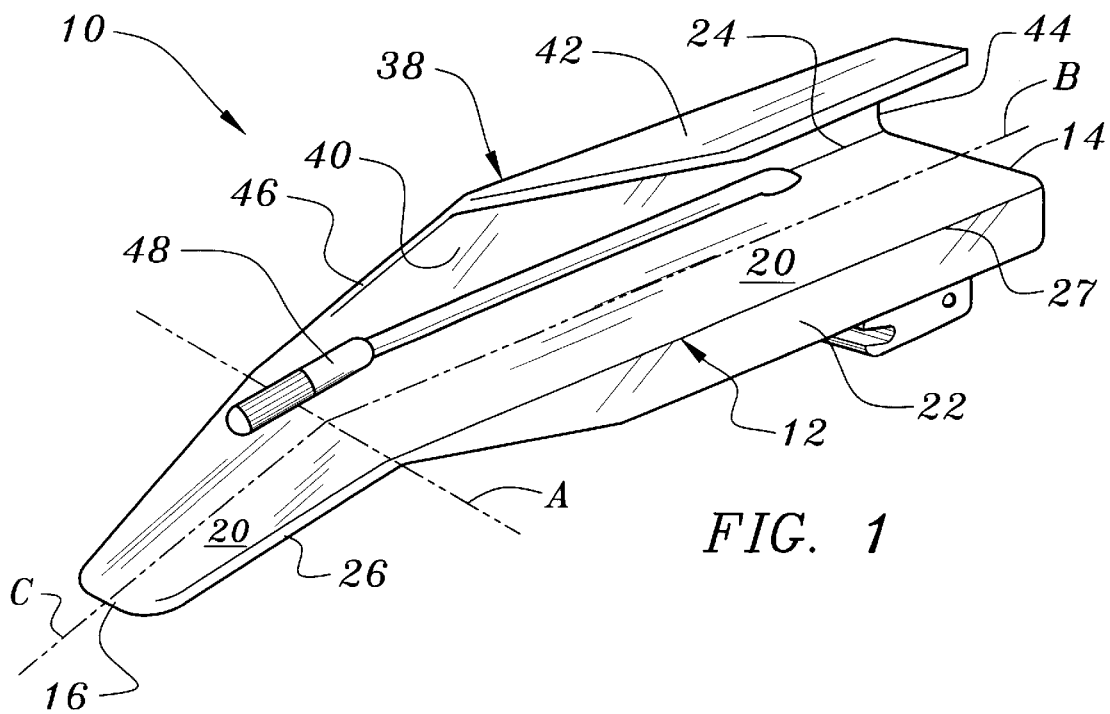
FIG. 1 is a front and right side isometric view of laryngoscope blade of this invention.
Figure 2:
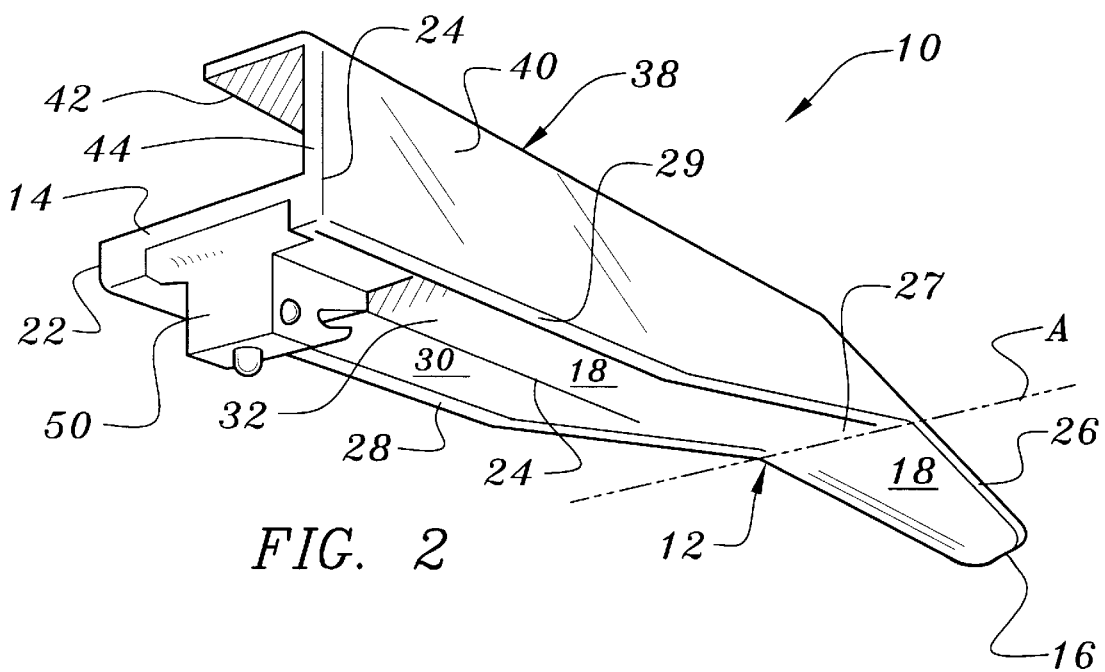
FIG. 2 is a rear and left side isometric view of laryngoscope blade of this invention.

A preferred embodiment for the laryngoscope blade of this invention is illustrated in the drawing FIGS. 1–8 in which the blade is generally indicated as 10. Referring first to the views of FIG. 1 and FIG. 2, it can be seen that the apparatus 10 comprises a longitudinally extending member 12 that has a first end 14, a second end 16, a lingual surface 18, a palatal surface 20, and a pair of opposed longitudinal edges 22 and 24. The member 12 comprises a first part 26, which includes the second end 16, and a second part 27, which includes the first end 14. As shown in FIG. 1 and 2, the first part 26 is angled back toward the lingual surface 18 along line A, which divides the first part 26 from the second part 27. Therefore, the longitudinal axis C of the first part 26 forms an angle of approximately 20 degrees with the longitudinal axis B of the second part 27 of the member 12. The longitudinal length from the first end 14 to line A is at least one-half the total longitudinal length of member 12 from the first end 14 to the second end 16. In a preferred embodiment, the longitudinal length of the first part 26 comprises approximately 25 percent of the total longitudinal length of member 12. In a preferred embodiment, the second part 27 of member 12 is flat, so that the major surfaces are essentially parallel and distinctly greater than the minor surfaces, that is the lingual and palatal surfaces, 18 and 20 respectively, are generally parallel to one another and are distinctly greater than the longitudinal edges 22 and 24. Thus the second part 27 of the member 12 has a generally constant thickness and the lingual surface 18 and the palatal surface 20 are planar. The first part 26 of the member 12 also has a generally constant thickness; however the lingual surface 18 and a palatal surface 20 are not necessarily planar. In a preferred embodiment, a portion of the first part 26 is concave in relation to the palatal surface 20. The curvature of this "spooned tip" generally fits the contour of the oropharynx of the patient being intubated. In a preferred embodiment, the longitudinal edges 22 and 24 of the first part 26 are tapered toward one another so that the second end 16 is narrower than the first end 14. In addition the second end 16 is rounded to reduce injury during insertion of the blade 10.

A pair of rails 28 extend outwardly from the lingual surface 18 of the member 12, being defined as rails 28 and 29, with one rail of the pair of rails being proximal to one of the pair of longitudinal edges and the other rail being proximal to the other longitudinal edge. As shown in FIG. 3, rail 28 is proximal to longitudinal edge 22 and rail 29 is proximal to longitudinal edge 24. In a preferred embodiment, each rail is flush with the corresponding longitudinal edge, as clearly seen in FIG. 2 and FIG. 3. As seen in FIGS. 3 and 5, the lingual surface 18 and the interior surfaces 30 and 31 of the rails 28 and 29 respectively, define a cavity 32. In a preferred embodiment, the interior surfaces 30 and 31 are perpendicular to the lingual surface 18. Rail 28 has a first end 34 and a second end 36 and rail 29 has a first end 35 and a second end 37. A portion of each rail 28 and 29, proximal to and including their respective second ends 36 and 37 are tapered toward the lingual surface 18 so that the second ends 36 and 37, as seen in FIGS. 2 and 3 are generally flush with the lingual surface 18.

An element 38, extends outwardly from the palatal surface 20 of the member 12 proximal to one of the longitudinal edges of the pair of longitudinal edges 22 and 24. In a preferred embodiment, the element 38 is attached to member 12 proximal to longitudinal edge 24, as seen in FIG. 1 and FIG. 2. A portion of the element 38 overlies and is spaced apart from the palatal surface. In a preferred embodiment, element 38 comprises a first leg 40 and a second leg 42. First leg 40 extends outwardly from and generally perpendicular to the palatal surface 20. The second leg 42 of element 38 is generally perpendicular to the first leg 40 and overlies the palatal surface and is generally parallel thereto. The element 38 has a first end 44 and a second end 46. A portion of the element 38 proximal to the second end 46 is tapered toward the palatal surface 20 so that the second end 44 of the first leg 40 is generally flush with the palatal surface 20.

A light source 48 is attached to the blade 10 so that it is focused away from the first end 14 of the blade, providing light within the oral cavity of the patient. The light source 48 is connected to a power supply (not shown) within a standard laryngoscope handle (not shown) that is attachable to the blade 10. A coupler 50,which is compatible with a standard laryngoscope handle, is attached to the first end 14 of the blade 10. for attachment of the blade 10 to a standard handle. When the blade 10 is attached to a handle it projects outwardly at generally a right angle to the lingual surface 18 of the blade 10. The coupler 50 is a standard well-known coupler that permits an electrical connection between the power source in the handle and the light source 48 on the blade The blade 10 is preferably constructed from stainless steel; but may be constructed from other suitable materials.

Having thus set forth a preferred construction for the current invention, is to the remembered that this is but a preferred embodiment. Attention is now invited to a description of the use of the blade 10. A practitioner may be called to intubate a patient that is either unconscious, awake and panicked or quietly awaiting surgery. Time is often critical as intubation provides an airway that is critical to the survival of the patient. The blades 10 come in a variety of sizes that are suitable for patients of varying ages and sizes. The practitioner must select a suitable blade 10 for the particular patient and then attach the blade 10 to a standard handle (not shown). The blade 10 is rotated until it forms approximately a 90 degree angle with the handle and a complete electrical connection is made between the power source and the light source 48. The practitioner inserts the blade 10 into the mouth of the patient with the lingual surface adjacent to the patient's tongue. A panicked patient, or even a calm one, will involuntarily fight intubation. One of the patient's most powerful tools to fight intubation is his tongue, which can push strongly against the blade 10 attempting to push it from his mouth. The main musculature of the tongue is central to the tongue and must be trapped in the cavity 32 between the rails 28 and 29 as the blade 10 is inserted. This cavity 32 an rails 28 and 29 prevent the tongue from "flowing over" the longitudinal edges of the blade 10 and into the line of sight. Also, as the blade is wider than prior art blades, it traps much of the tongue within the cavity 32 without having to apply excessive lift force, which can cause injury to the patient. Often the tissues of the airway, oropharynx, and epiglottis are swollen and obscure the line of sight. The wide blade with the cavity 32 enables the practitioner to trap the excess tissue within the cavity 32.

The rounded tip, or first end 16, of the blade 10 is extended into the oropharynx to lift the epiglottis out of the line of sight. The first end 16 of the blade being concave, is curved so that it matches the generally cylindrical oropharynx area reducing injury to the tissue of the patient's oropharynx.

To ensure a direct view of the oropharynx and the vocal cords, the patient's mouth must be open relatively wide. Therefore the height of the blade 10, that is the spacing between the palatal surface 20 and the second leg 42, is important as it spaces the lower teeth from the upper teeth of the patient. The practitioner then may feed the endotracheal tube through this space, between the second leg 42 and the palatal surface 20, and into the patient's oropharynx, between his vocal cords and into his trachea. The second part 27 of the member 12 is straight and planar providing a direct view of the vocal cords, which would be much more difficult if the blade were curved. The blade 10 produces a direct line of sight to the epiglottis and vocal cords without excess manipulation that costs time and causes undue trauma to the patient.

While the foregoing describes the structure of a particularly preferred embodiment of the present invention, it is to be understood that numerous variations and modifications of the structure will occur to those skilled in the art. Accordingly, the foregoing description is to be considered illustrative only of the principles of this invention and is not to be considered limitative thereof, the scope of the invention being determined solely by the claims appended hereto.

What is claimed is:

1. A laryngoscope blade comprising:

a longitudinally extending member having a first end, a second end, a lingual surface, a palatal surface, and a pair of opposed longitudinal edges, a portion of said member, over one half of the longitudinal length of said member being straight and over one half of said longitudinal length of said lingual surface being generally planar;

a pair of rails extending outwardly from said planar lingual surface, one of said pair of rails being proximal to one of said pair of longitudinal edges of said member, and the other one of said pair of rails being proximal to the other one of said pair of longitudinal edges;

an element extending outwardly from said palatal surface of said member proximal to one of said pair of longitudinal edges of said member, a portion of said element overlying and spaced apart from said palatal surface; and a coupler attached to said first end of said member, whereby said blade is attachable to a handle.

2. A laryngoscope blade as in claim 1 wherein each rail of said pair of rails has an interior surface and said interior surface of each said rail extends outwardly from and at generally right angles to said planar lingual surface.

3. A laryngoscope blade as in claim 1 wherein said member further comprises a first part that includes said second end of said member and a second part that includes said first end of said member, said first part being angled, in relation to said second part of said member, toward said lingual surface of said second part of said member.

4. A laryngoscope blade as in claim 3, wherein said first part of said member is concave in relation to said palatal surface such that the contour of said second end of said member generally corresponds to said contour of the oropharynx when said second end of said member is received therein.

5. A laryngoscope blade as in claim 1 wherein said rails have a first end and a second end, a portion of said rails proximal to said second end of said rails being tapered toward said lingual surface such that said second end of said rails are generally flush with said lingual surface.

6. A laryngoscope blade as in claim 1 wherein said element has a first and a second end, a portion of said element proximal said second end being tapered toward said palatal surface such that said second end of said element is generally flush with said palatal surface.

7. A laryngoscope blade as in claim 1 wherein said longitudinal edges of said member proximal said second end are tapered toward one another and said second end is rounded.

* * * * *